United States Patent
Rahman et al.

(10) Patent No.: US 9,381,364 B2
(45) Date of Patent: Jul. 5, 2016

(54) TELEMETRY OPTIMIZATION IN AN IMPLANTABLE MEDICAL DEVICE SYSTEM TO ACHIEVE EQUAL AND MAXIMAL DISTANCES IN BIDIRECTIONAL COMMUNICATIONS

(75) Inventors: Md. Mizanur Rahman, Stevenson Ranch, CA (US); Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 363 days.

(21) Appl. No.: 13/222,112

(22) Filed: Aug. 31, 2011

(65) Prior Publication Data

US 2012/0095744 A1  Apr. 19, 2012

Related U.S. Application Data

(60) Provisional application No. 61/393,980, filed on Oct. 18, 2010.

(51) Int. Cl.
*G06F 17/50* (2006.01)
*A61N 1/372* (2006.01)
(Continued)

(52) U.S. Cl.
CPC .......... *A61N 1/37223* (2013.01); *H04B 5/0081* (2013.01); *H04B 5/0087* (2013.01); *H04B 17/27* (2015.01); *A61N 1/37229* (2013.01);
(Continued)

(58) Field of Classification Search
CPC ........... A61N 1/37223; A61N 1/37229; A61N 1/3962; A61N 1/3956; H04B 17/0072; H04B 5/0087; H04B 5/0031; H04B 5/0037; H04B 5/0093; H04B 5/0043; H04B 5/0081; G06F 17/5063; G06F 17/50; G06G 7/62
USPC .......... 703/14, 13; 607/60, 32, 59, 30; 348/77
See application file for complete search history.

(56) References Cited

U.S. PATENT DOCUMENTS 6,516,227 B1   2/2003  Meadows et al.
2008/0319349 A1*  12/2008  Zilberman .................... 600/587
(Continued)

OTHER PUBLICATIONS

Jow, Uei-Ming et al., "Optimization of a Multiband Wireless Link for Neuroprostetic Implantable Devices", 2008, IEEE.*
(Continued)

*Primary Examiner* — Cedric D Johnson
(74) *Attorney, Agent, or Firm* — Lewis, Reese & Nesmith, PLLC

(57) ABSTRACT

Methods for optimizing telemetry in an implantable medical device system are disclosed, with the goal of equating and maximizing the communication distances between devices in the system, such as the external controller and the Implantable Pulse Generator (IPG). The method involves computerized simulation of maximum communication distances in both directions between the two devices while varying at least two parameters of the telemetry circuitry, such as the number of turns in the telemetry coils in the two devices. This results in a simulation output comprising a matrix in which each element comprises the bidirectional distance values. An element is determined for which the distances are equal (or nearly equal) and maximized (or nearly maximized), and the optimal values for the parameters are then chosen on that basis, with the result that the communication distance in one direction equals the communication distance in the other direction, and is maximized.

21 Claims, 9 Drawing Sheets

(51) Int. Cl.
*H04B 5/00* (2006.01)
*H04B 17/27* (2015.01)

(52) U.S. Cl.
CPC ........... *G06F17/5063* (2013.01); *H04B 5/0031* (2013.01); *H04B 5/0037* (2013.01)

(56) References Cited

U.S. PATENT DOCUMENTS

| | | | |
|---|---|---|---|
| 2009/0024179 A1 | 1/2009 | Dronov | |
| 2009/0259273 A1* | 10/2009 | Figueiredo et al. | 607/32 |
| 2009/0281597 A1 | 11/2009 | Parramon et al. | |
| 2010/0228324 A1 | 9/2010 | Lamont et al. | |

OTHER PUBLICATIONS

Ghovanloo, Maysam et al., "A Wide-Band Power-Efficient Inductive Wireless Link for Implantable Microelectronic Devices Using Multiple Carriers", Oct. 2007, IEEE Transactions on Circuits and Systems, I: Regular papers, vol. 54, No. 10, IEEE.*

Yang, Cao et al., "Secure Method for Software Upgrades for Implantable Medical Devices", Oct. 2010, Tsinghua Science and Technology, vol. 15, No. 5.*

Jow, Uei-Ming et al., "Optimization of Data Coils in a Multiband Wireless Link for Neuroprosthetic Implantable Devices", Oct. 2010, IEEE Transactions on Biomedical Circuits and Systems, vol. 4, No. 5, IEEE.*

Schulman J.H. et al., "Battery Powered BION FES Network", Sep. 1-5, 2004, Proceedings of the 26th Annual International Conference of the IEEE EMBS, IEEE.*

Rehfub, S. et al., "Modeling and Optimization of Micro Coils for Telemetric Transmission at Frequencies up to 20 MHz", Mar.-Apr. 1999, Symposium on Design, Test, and Microfabrication of MEMS and MOEMS, SPIE.*

Sauer, Christian et al., "Power Harvesting and Telemetry in CMOS for Implanted Devices", Dec. 2005, IEEE Transactions on Circuits and Systems, vol. 52, No. 12, IEEE.*

Wang, Guoxing et al., "A Dual Band Wireless Power and Data Telemetry for Retinal Prosthesis", Aug. 30-Sep. 3, 2006, Proceedings of the 28th IEEE EMBS Annual International Conference, IEEE.*

Wang, Guoxing et al., "Design and Analysis of an Adaptive Transcutaneous Power Telemetry for Biomedical Implants", Oct. 2005, IEEE Transactions on Circuits and Systems—I: Regular Papers, vol. 52, No. 10, IEEE.*

Sawan, Mohamad et al., Multicoils-Based Inductive Links Dedicated to Power Up Implantable Medical Devices: Modeling, Design and Experimental Results, Jun. 2, 2009, Biomed Microdevices, Springer.*

International Search Report and Written Opinion regarding corresponding PCT application No. PCT/US2011/054872, dated Feb. 7, 2012.

G. Wang et al.; "A Dual Band Wireless Power and Data Telemetry for Retinal Prosthesis;" Proceedings of the 28th IEEE EMBS Annual International Conference; Aug. 30-Sep. 3, 2006; p. 4392-4395; 1-4244-0033-3/06; New York City, USA.

M. Ghovanloo et al.; "A Wide-Band Power-Efficient Inductive Wireless Link for Implantable Microelectronic Devices Using Multiple Carriers;" IEEE Transactions on Circuits and Systems-I: Regular Papers; Oct. 2007; p. 2211-2221; vol. 54; No. 10; USA.

J. Coosemans et al.; "Integrating Wireless ECG Monitoring in Textiles;" Sensors and Actuators A 130-131 (2006); ; www.elsevier.com/locate/sna; Jun. 20, 2005; p. 48-53.

M. Zimmerman, et al.; "In Vivo RF Powering for Advanced Biological Research;" Proceedings of the 28th IEEE EMBS Annual International Conference; Aug. 30-Sep. 3, 2006; p. 2506-2509; 1-4244-0033-3106; New York City, USA.

* cited by examiner

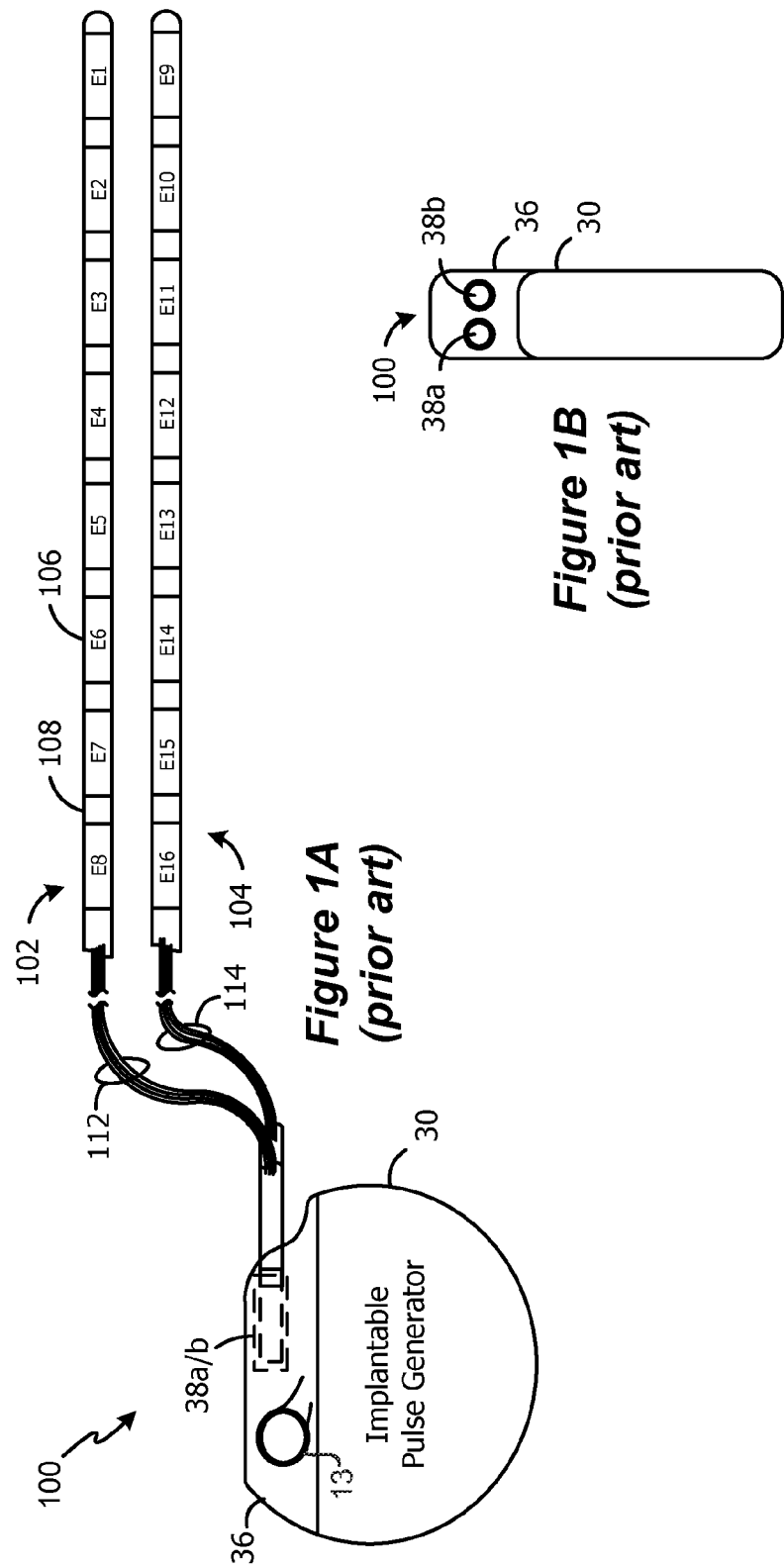

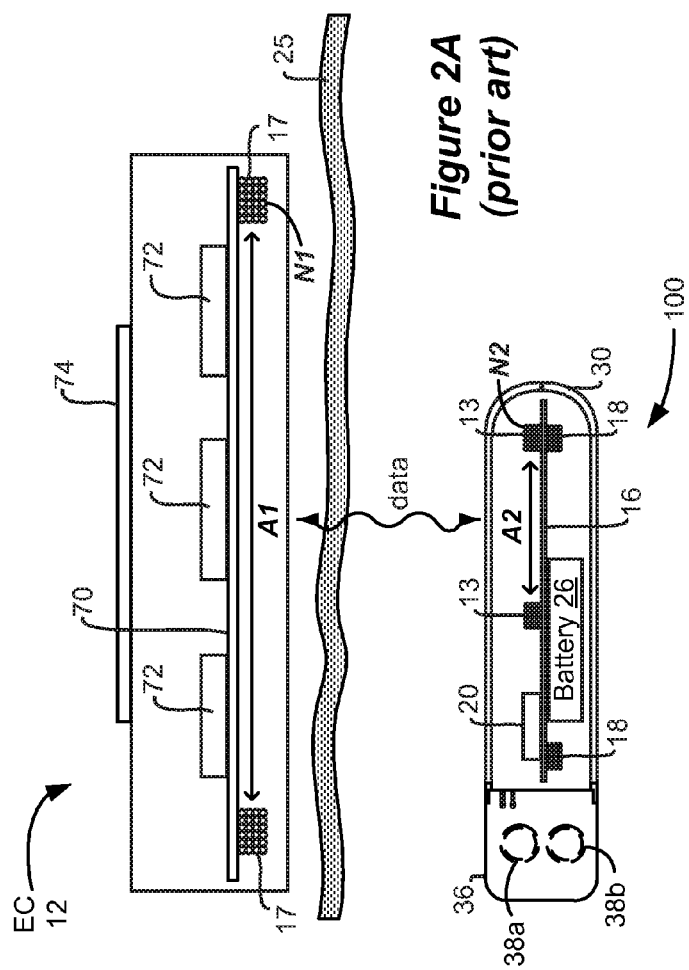
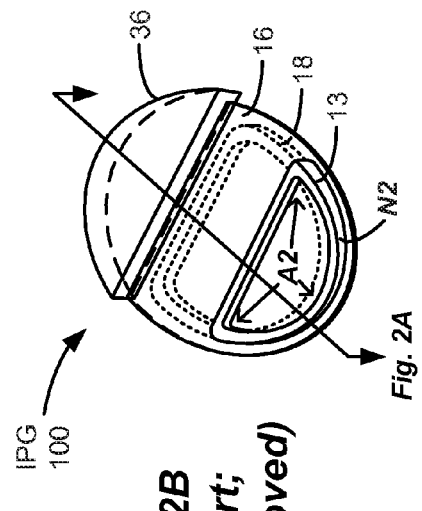
*Figure 2A (prior art)*
*Figure 2B (prior art; case removed)*

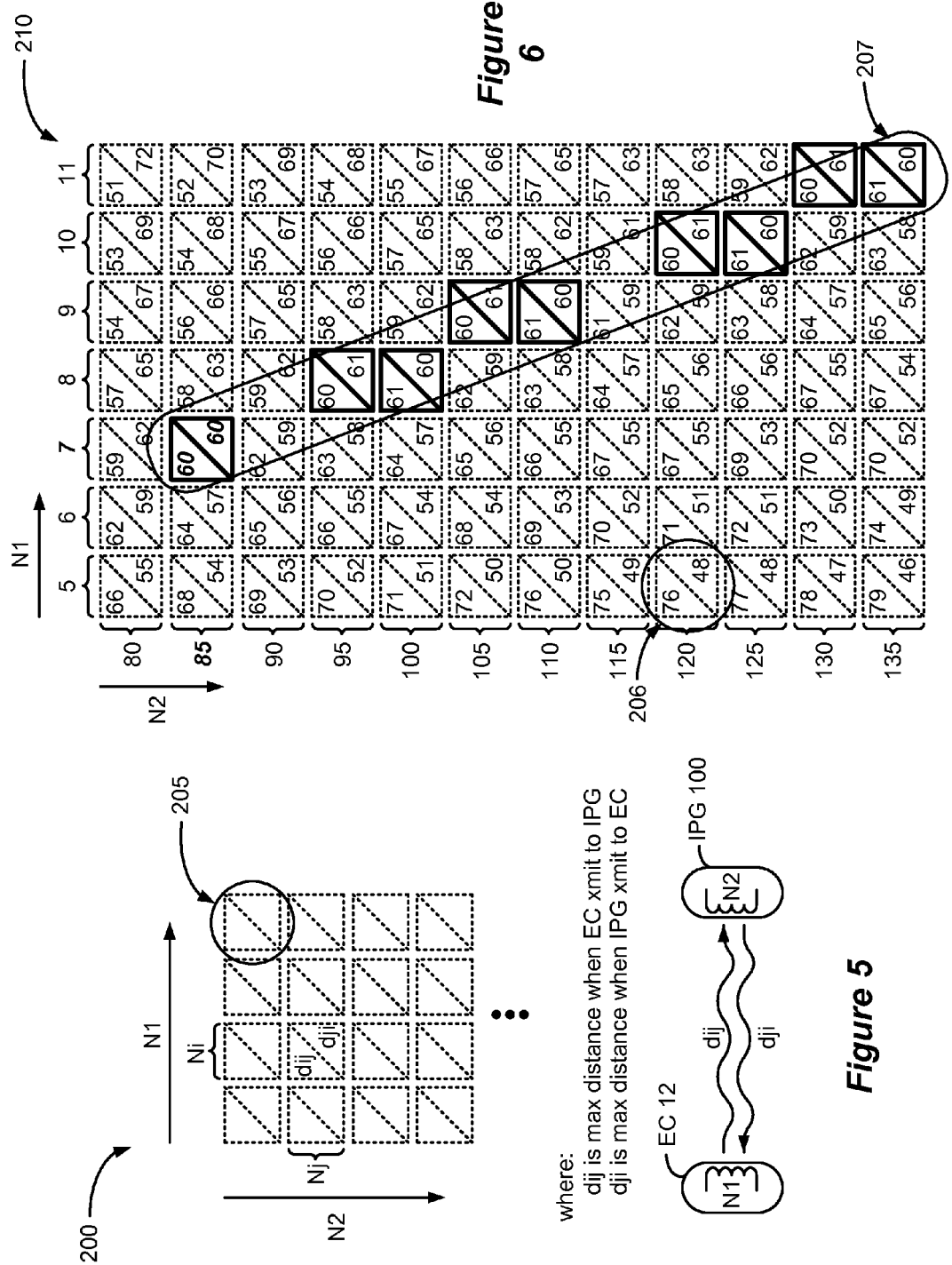

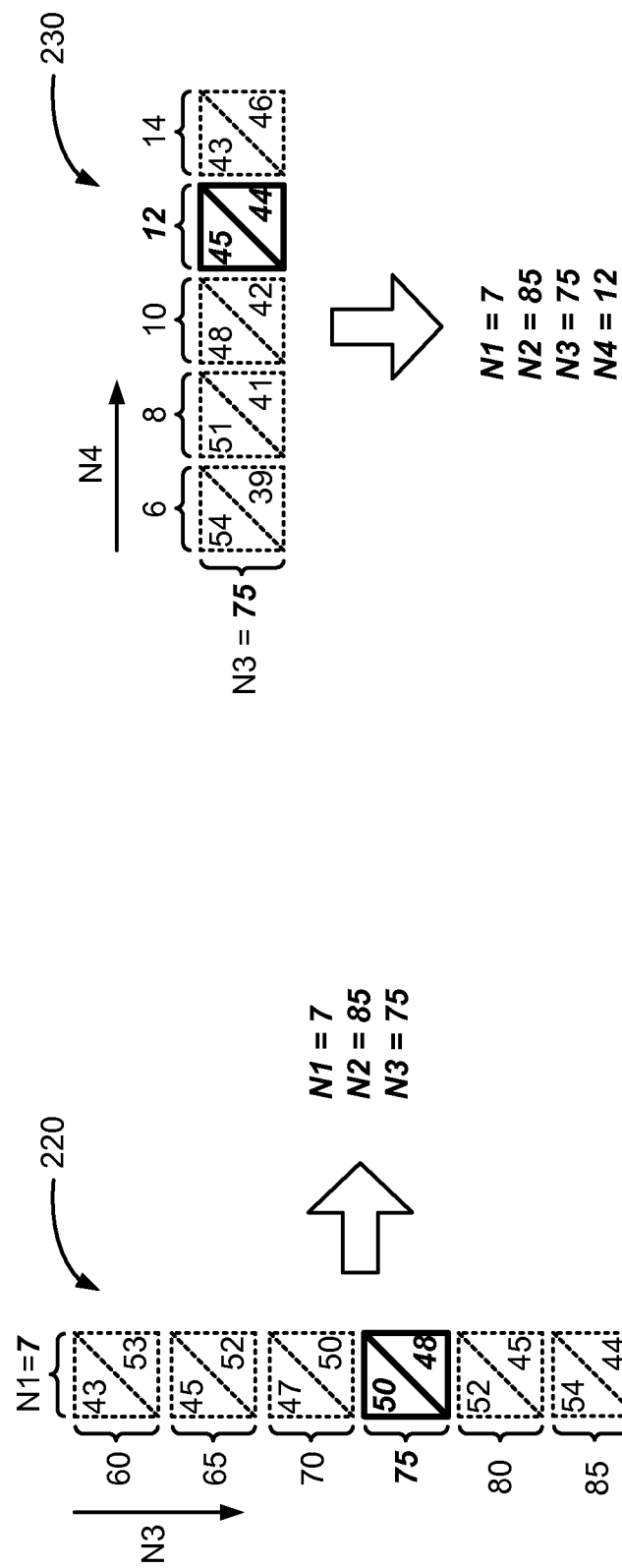

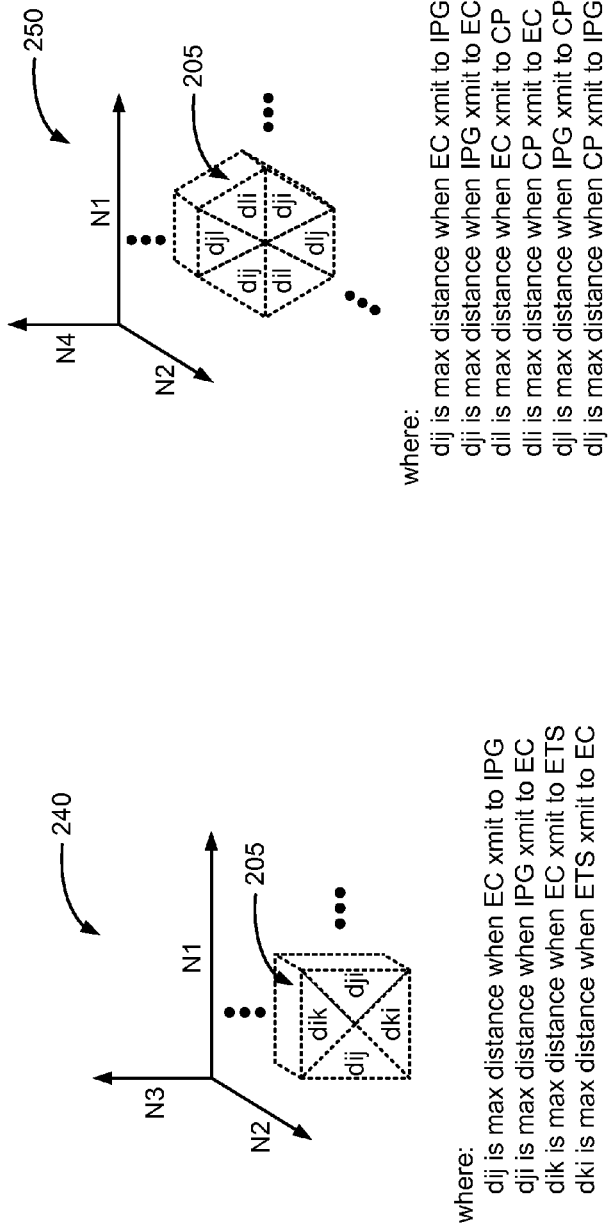
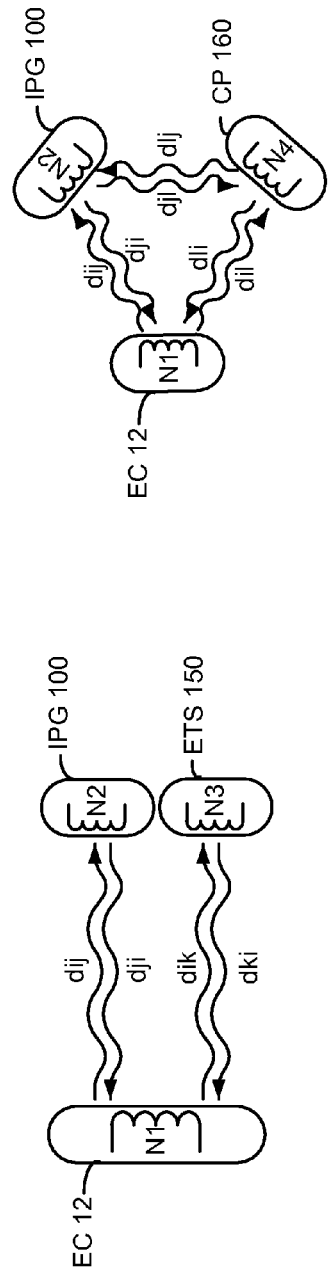
Figure 9A
Figure 9B

US 9,381,364 B2

TELEMETRY OPTIMIZATION IN AN IMPLANTABLE MEDICAL DEVICE SYSTEM TO ACHIEVE EQUAL AND MAXIMAL DISTANCES IN BIDIRECTIONAL COMMUNICATIONS

CROSS REFERENCE TO RELATED APPLICATIONS

This is a non-provisional application of U.S. patent application Ser. No. 61/393,980, filed Oct. 18, 2010, to which priority is claimed, and which is incorporated herein by reference in its entirety.

FIELD OF THE INVENTION

The present disclosure relates to optimization of telemetry in an implantable medical device system.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A and 1B, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 includes one or more electrode arrays (two such arrays 102 and 104 are shown), each containing several electrodes 106. The electrodes 106 are carried on a flexible body 108, which also houses the individual electrode leads 112 and 114 coupled to each electrode. In the illustrated embodiment, there are eight electrodes on array 102, labeled $E_1$-$E_8$, and eight electrodes on array 104, labeled $E_9$-$E_{16}$, although the number of arrays and electrodes is application specific and therefore can vary. The arrays 102, 104 couple to the IPG 100 using lead connectors 38a and 38b, which are fixed in a non-conductive header material 36, which can comprise an epoxy for example.

As shown in cross-section in FIG. 2A, the IPG 100 typically includes an electronic substrate assembly including a printed circuit board (PCB) 16, along with various electronic components 20, such as microprocessors, integrated circuits, and capacitors mounted to the PCB 16. Two coils (more generally, antennas) are generally present in the IPG 100: a telemetry coil 13 used to transmit/receive data to/from an external controller 12; and a charging coil 18 for charging or recharging the IPG's battery 26 using an external charger (not shown). The telemetry coil 13 can be internal to the case 30 as shown, or can alternatively be placed in the header 36.

As just noted, an external controller (EC) 12 is used to wirelessly send data to and receive data from the IPG 100. For example, the EC 12 can send programming data to the IPG 100 to dictate the therapy the IPG 100 will provide to the patient. Also, the EC 12 can act as a receiver of data from the IPG 100, such as various data reporting on the IPG's status. The EC 12, like the IPG 100, also contains a PCB 70 on which electronic components 72 are placed to control operation of the EC 12. A user interface 74 similar to that used for a computer, cell phone, or other hand held electronic device, and including touchable buttons and a display for example, allows a patient or clinician to operate the EC 12. The communication of data to and from the EC 12 is enabled by a coil (antenna) 17.

Wireless data telemetry between the EC 12 and the IPG 100 takes place via inductive coupling, and specifically magnetic inductive coupling. To implement such functionality, both the IPG 100 and the EC 12 have coils 13 and 17 which act together as a pair. When data is to be sent from the EC 12 to the IPG 100 for example, coil 17 is energized with an alternating current (AC). Such energizing of the coil 17 to transfer data can occur using a well-known Frequency Shift Keying (FSK) protocol for example. See, e.g., U.S. Patent Publication 2009/0024179. Inductive transmission of data can occur transcutaneously, i.e., through the patient's tissue 25, making it particularly useful in a medical implantable device system. During the transmission of data, the coils 17 and 13 preferably lie in planes that are parallel, along collinear axes, and with the coils as close as possible to each other, as is generally shown in FIG. 2A. Such an orientation between the coils 17 and 13 will generally improve the coupling between them, but deviation from ideal orientations can still result in suitably reliable data transfer.

FIG. 3 shows further details of the telemetry circuitry in the EC 12 and the IPG 100. Although the telemetry circuitry in these devices may have significant differences in a real application, for the purpose of FIG. 3 such circuitry is illustrated simply, and can be viewed as essentially the same in both devices.

As shown, the EC 12 contains a transmitter TX1 for transmitting a serial stream of digital data (DATA_TX1) to the IPG 100. The transmitter TX1 contains well-known modulation circuitry to modulate the data to an appropriate frequency in accordance with the FSK protocol used. The modulated data is presented to the resonant circuitry (or "tank circuitry") in the external controller, which consists of an L-C circuit made up of a capacitor and the inductance of the telemetry coil 17. The resonant circuit can comprise a parallel or series connection between the capacitance and the inductance. In one example, a series L-C connection is used when a device is transmitting data, while a parallel L-C connection is used when the device is receiving data. Such dual-mode telemetry circuitry, and rationales for switching between a series and parallel connection depending on whether the circuit is transmitting or receiving, can be found in U.S. Patent Publication 2009/0281597, which is incorporated herein by reference. This Publication is assumed familiar to the reader, and hence its details are not reflected in the circuitry of FIG. 3; instead, the capacitor is shown in dotted lines both in series and in parallel with the inductance of the coil, denoting that it could be in either orientation depending on the circumstances.

The modulated data is presented to the resonant circuitry as an output voltage, Vo1, which in reality comprises rapidly alternating +Vo1 and −Vo1 voltages to provide resonance at the desired FSK frequencies. Stimulating the resonant circuitry in this fashion creates a modulated AC magnetic field, which field is then sensed by at the telemetry coil 13 in the IPG 100. Specifically, the magnetic field induces a current in the coil 13, which ultimately forms a voltage Vi2 across the resonant L-C circuit in IPG 100. Again, the polarity of Vi2 alternates depending on the frequency of transmission. This input voltage Vi2 is presented to a receiver RX2, where it is demodulated to recover the digital data stream (DATA_RX2).

Data transmission from the IPG 100 to the external controller 12 occurs in much the same manner. Digital data (DATA_TX2) is modulated in a transmitter TX2 in the IPG 100, which modulates the data to particular FSK frequencies. The resulting output voltage Vo2 is presented across the resonant circuit formed by a capacitor and the inductance of the telemetry coil 13. The resulting magnetic field is sensed at the telemetry coil 17 in the external controller, and the resulting input voltage Vi1 that forms across the resonant circuit is demodulated to recover the digital data stream (DATA_RX1).

Both of the telemetry coils 17 and 13 are roughly circular, as can be seen in FIGS. 2A and 2B, and each is generally comprised of several windings of wire. As such, each coil 17 and 13 is characterized by an area (A, the area encompassed by the coil) and a number of turns (N, the number of turns of the copper wire used to form the coils). The telemetry circuitry in each device is further characterized by its transmitter output voltage Vo, and its minimum receiver input voltage Vi. This disclosure addresses optimization of such parameters to improve communication distance and reliability between the external controller and the IPG, or between other devices in the implantable medical device system that will be intruded later.

BRIEF DESCRIPTION OF THE DRAWINGS

FIGS. 1A and 1B show an implantable medical device, and the manner in which an electrode array is coupled to the IPG in accordance with the prior art.

FIGS. 2A and 2B show the relation between the implantable medical device and an external controller in accordance with the prior art.

FIG. 5 shows a simulation output comprising a matrix with elements comprised of distance values, the matrix useable in the selection of an optimal number of turns for the communication coils in the external controller and the IPG to achieve equal and maximum distances in bidirectional communications.

FIG. 6 shows the simulation output from an actual computerized simulation, leading to the selection of a particular number of turns for the coils in the external controller and the IPG.

FIGS. 8A and 8B show simulation outputs useable to select the number of turns for the coils in the external trial stimulator and the clinician programmer once the number of turns of the coils in the external controller and IPG have been selected in FIG. 6.

FIGS. 9A and 9B shows simulation outputs useable to select a number of coils to simultaneously optimize bidirectional communications in three devices in an implantable medical device system.

DETAILED DESCRIPTION

The description that follows relates to use of the invention within spinal cord stimulation (SCS) system. However, it is to be understood that the invention is not so limited, and could be used with any type of implantable medical device system.

Figure 3:
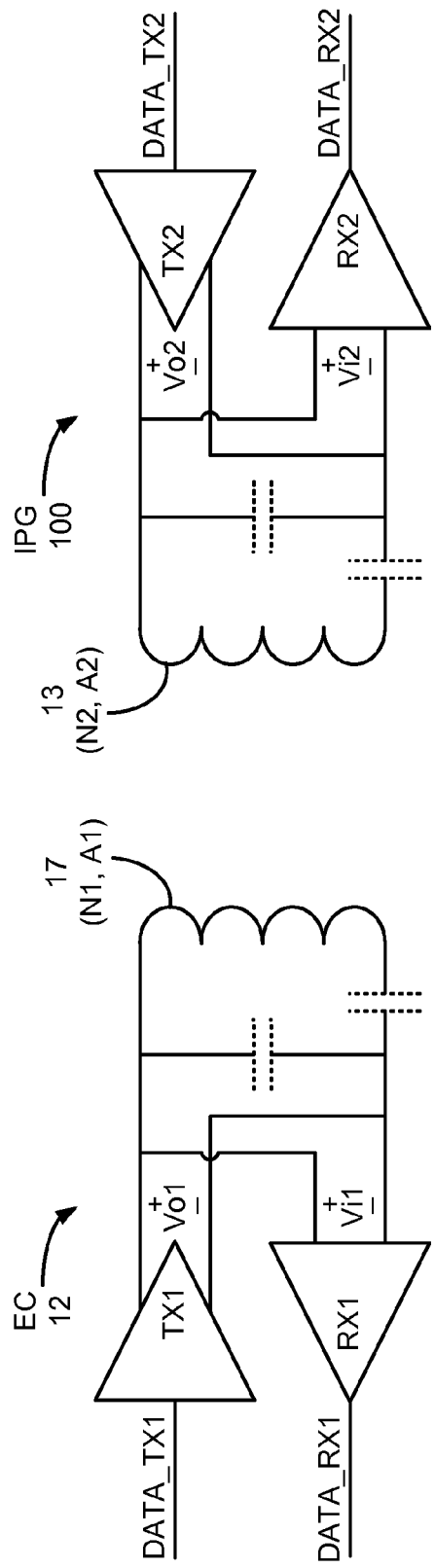
FIG. 3 shows aspects of the telemetry circuitry in the external controller and the IPG in accordance with the prior art.

As noted earlier, and as shown in FIGS. 2A, 2B, and 3, the telemetry circuitry in the EC 12 and the IPG 100 are characterized by various parameters. Generally in the prior art these parameters were chosen to optimize some particular issue in the IPG system. However, the inventors believe that optimization of such parameters has not considered optimization of communications in both directions—i.e., when transmitting from the external controller to the IPG and vice versa.

Figure 4A:
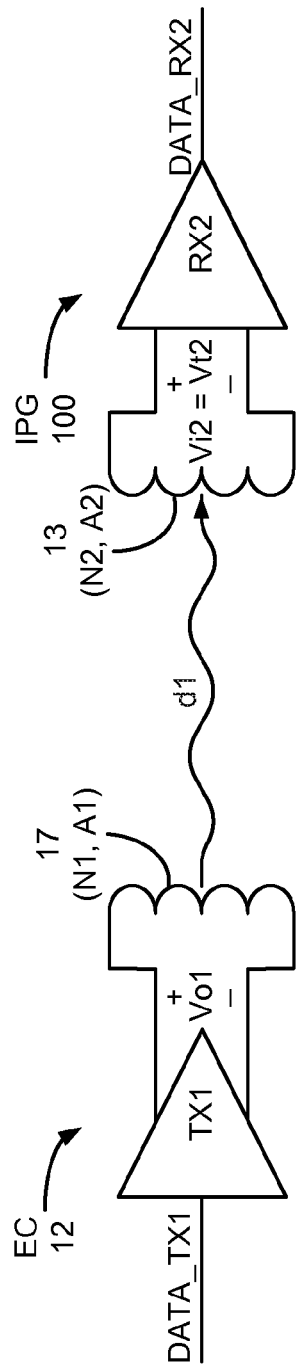
FIGS. 4A and 4B show how the telemetry circuitry of the prior art does not necessarily result in equal communication distances in both directions between an external controller and an IPG.
Figure 4B:
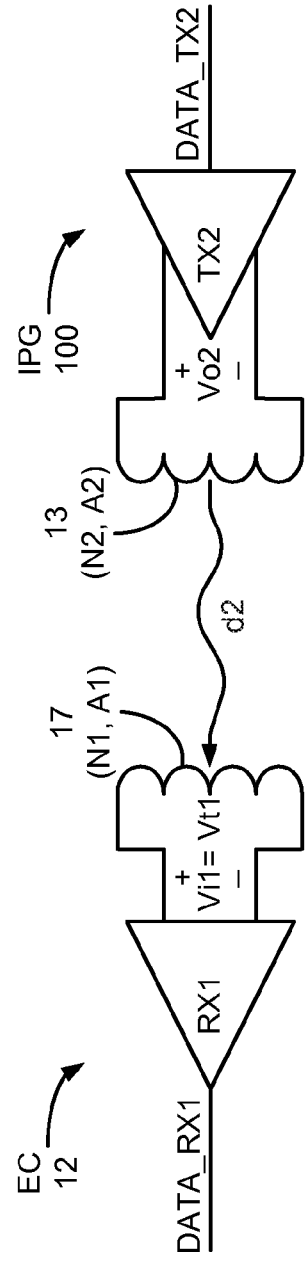

Failure to optimize bidirectional communications is shown in FIGS. 4A and 4B. FIG. 4A shows the transmission of data from the EC 12 to the IPG 100, borrowing relevant circuitry from FIG. 3. (The capacitor in the resonant circuit has been omitted for clarity). Specifically shown in the EC 12 are some of the parameters for the transmitter circuitry discussed previously, including the transmitter's output voltage Vo1 and the area A1 and number of turns N1 of the coil 17. If one assumes that these parameters are constant, the EC 12 will emit a magnetic field of a particular strength. This magnetic field can be said to have a maximum distance d1, which can be defined as the largest distance at which the receiver circuitry in the IPG 100 can reliably sense the magnetic field. In this regard, note that the receiver RX2 in the IPG 100 can generally be characterized as having a minimum voltage input or threshold, Vt2, at which it can reliably resolve and demodulate the incoming data. Thus, when the input voltage Vi2 to the receiver RX2 equals Vt2, the maximum distance d1 is defined. Should the IPG 100 be positioned farther than d1 from the EC 12, Vi2 would be less than Vt2, and communications would be unreliable or unresolvable. Vi2 is affected by parameters in the receiving circuitry, such as A2 and N2, which in turn will affect the maximum distance d1. In the example shown, maximum distance d1 is illustrated assuming the coils 17 and 13 are collinear and wrapped in planes that are parallel to each other, as shown in FIG. 2A for example. Such assumptions will maximize the coupling between the coils 17 and 13, and hence maximize the maximum distance d1.

FIG. 4B is similar to FIG. 4A, but with telemetry in the opposite direction—from the IPG 100 to the EC 12. The same coil parameters N1, N2, A1, and A2 are assumed, and once again the maximum distance d2 is assessed. This assessment is similar to what was just described: assuming a particular transmitter output voltage Vo2 from the IPG 100, and a particular area (A2) and number of turns (N2) for the telemetry coil 13, a magnetic field is produced. That magnetic field produces an input voltage Vi1 at the receiver RX1 in the EC 12, which input voltage is affected by A1 and N1, and which when equal to the receiver's threshold Vt1 defines the maximum distance, d2. Notice however that the maximum distance d2 in FIG. 4B is smaller than the maximum distance d1 in FIG. 4A. This can arise for many reasons. For example, the voltage Vo2 output from transmitter TX2 in the IPG 100 may be different from the voltage Vo1 output from transmitter TX1 in the EC 12. Or, the receivers RX1 and RX2 may be differently constructed, or have different threshold voltages Vt1 and Vt2.

Another reason that the maximum distances d1 and d2 may be different relates to the differences in configuration of the telemetry circuitry. Consider for example if the IPG 100 uses dual-mode telemetry circuitry which is configured differently for transmission and reception, as disclosed in U.S. Patent Publication 2009/0281597. When receiving, the inductance of the telemetry coil 13 in the IPG 100 is coupled in parallel with a capacitor. Without belaboring the physics, the input voltage Vi2 to the IPG 100 receiver RX2 will vary roughly proportionally with the number of turns (N2). Therefore, to maximize Vi2, and in turn increase maximum distance d1, the number of turns N2 of the coil 13 could be increased. By contrast, when transmitting, the inductance of the telemetry coil 13 is coupled in series with the capacitor. Again without belaboring the physics, the magnitude of the magnetic field produced by the transmitter TX2, as represented by output voltage Vo2, will vary roughly inversely with the number of turns (N2) of the coil 13. Therefore, to maximize Vo2, and in turn increase maximum distance d2, the number of turns N2 of the coil 13 could be decreased, contrary to what is indicated when increasing d1.

Regardless of the cause of the difference in maximum distances d1 and d2, such difference is regrettable because it affects bidirectional communications between the EC 12 and the IPG 100. If these devices are located at a distance between d1 and d2, communication can only be had in one direction, which prevents the clean flow of information between the two. To ensure reliable bidirectional communications, the devices must be located at a distance no further than d2—the smaller of the two distances. But this distance d2 may not be optimized, and may be too small.

This disclosure provides a methodology for optimizing bidirectional communications in an implantable medical device system using computerized simulations. In particular, most of the simulations illustrated are directed to optimizing the number of turns (n) in the EC 12, the IPG 100, and in other devices in a broader implantable medical device system as well. As will be seen in the simulations that follow, optimizing the number of coil turns in these devices maximizes the distance of bidirectional communications in both directions.

Optimizing the number of coils turns is generally preferred compared to the optimization of other parameters in the system (e.g., coil area, Vo, Vt) because these others parameters may be difficult to change given other system constraints. Vo may be constrained by the power available at the transmitting device, and Vi may be hard to adjust without a redesign of the receivers RX. By contrast, the number of turns of the coils 13 and 17 may be relatively easy to change, and moreover has been noted by the inventors as a parameter particularly in need of optimization when dual-mode telemetry circuitry is used in either or both of the EC 12 or the IPG 100. As noted earlier, the physics of such circuitry suggests that the number of coil turns should be increased for reception but decreased for transmission, suggesting that optimization of this variable is particularly appropriate.

FIG. 5 shows the basic structure of the output 200 of a computer simulation designed to optimize the number of turns N1 and N2 in the EC 12 and the IPG 100 respectively. As can be seen, the simulation output 200 as illustrated comprises a 2 dimensional matrix in which N1 and N2 varies. Each element 205 of the matrix 200 comprises two values, dij and dji for a given number of turns in the EC 12 (Ni) and in the IPG 100 (Nj). dij comprises the simulated maximum distance when telemetering from the EC 12 to the IPG 100, while dji comprises the simulated maximum distance when telemetering in the other direction from the IPG 100 to the EC 12.

Simulated distances dij and dji can be arrived at in many different ways as one skilled in the art will understand. Sophisticated simulator programs can be used, such as the HFSS 3D full-wave electromagnetic field software program produced by Ansys, Inc., or the EMPro 3D EM simulation software program produced by Agilent Technologies. The use of such programs will allow the full structure of the external controller/IPG environment to be modeled, including factors causing non-idealities in the production and reception of the magnetic field such as the housing and other conductive structures in the EC 12 and the IPG 100. Or less sophisticated computational software can also be used such as Matlab™ or Excel™, although the use of such programs may require the designer to make additional assumptions about the external controller/IPG environment, or to simplify that environment. Combinations of these or other software programs can also be used to arrive at dij and dji. In any event, the goal of such simulation is to determine the maximum distance at which the voltage induced on the receiving coil (Vi) equals the known threshold voltages of its receiver (Vt), as explained earlier. Such simulation would logically assume that the coils 17 and 13 in the EC 12 and the IPG 100 are collinear and wrapped in planes that are parallel to each other, which as noted earlier will maximize coupling. Simulation can take place in a computer system, which can comprise a single workstation, or any other combination and connection of computing devices.

FIG. 6 shows the output of an actual simulation 210 run for a system in which the EC 12 and IPG 100 both have dual-mode telemetry circuitry. However, this is not strictly necessary, and the EC 12 can comprise a resonant circuit that is always serially connected in both transmit and receive modes. The simulation output 210 is preferably captured in the same computer system that performs the simulation. Capturing the simulation output 210 in a computer system is beneficial because it allows the output to be at least partially automatically analyzed according to criteria discussed below.

The simulation underlying simulation output 210 assumed an external controller coil 17 area A1 of 24 $cm^2$ and an IPG coil 13 area A2 of 2.5 $cm^2$. The threshold voltage Vt1 of the receiver RX1 in the external controller was assumed to be 10 μV, while the threshold voltage Vt2 of the receiver RX2 in the IPG was assumed to be 600 μV. The output voltage Vo1 of the transmitter TX1 in the external controller was assumed to be 3.4 V, while the output voltage Vo2 of the transmitter TX2 in the IPG was assumed to be 2.9 V. For simplicity, the simulation did not consider the housings or other structures of the EC 12 or IPG 100, and assumed coils in free space. Simulation was run using Matlab on a standard work station, which used well-known formulas to calculate magnetic field strength generated by the transmitting coil as a function of distance, and the voltage Vi that such magnetic field impressed on the receiving coil.

Distances dij and dji were calculated for each element in the matrix 210, i.e., for each N1/N2 pair. It can be seen that N1 and N2 were limited to particulars ranges, with N1 (the number of turns in the external controller) varying between 5 and 11 turns, and N2 (the number of turns in the IPG) varying between 80 and 135 turns. Such ranges for the number of turns will be limited to what is mechanically and electrically practical for the devices in question, and perhaps with some preliminary knowledge as to where the optimal number of turns would be expected as deduced from experimentation or testing.

Simulation output 210 illustrates mismatched communication distances discussed earlier. Take for example matrix element 206, corresponding to N1=5 turns and N2=120 turns. The maximum distance when transmitting from the EC 12 to the IPG 100 for these values is 76 inches, but only 48 inches when transmitting in the other direction. This difference in distances is not desirable for the reasons stated earlier, and so the simulation output 210 does not reflect that design an EC 12 with a coil with 5 turns, and an IPG 100 with a coil of 120 turns would be ideal.

By contrast, simulation output 210 exhibits a range 207 in which the distance values for each element are the closest— i.e., where the values match, or nearly match, and such elements have been bolded for easy viewing. In each of these elements, the maximum distances in both directions roughly equal 60-61 inches. The number of turns corresponding to these elements would be ideal to support bidirectional communication between the EC 12 and the IPG 100, and the most ideal of the elements would be that in which the equivalent distances are highest. However, no particular highest equal distances are reflected by the elements in range 207, so any of these elements would suggest an ideal number of turns. Still, from the range 207, a most ideal value could be chosen on the basis of other considerations. For example, choosing the fewest number of turns would be simplest to manufacture. On this basis, simulation output 210 suggest that the most ideal value would comprise an EC 12 with a coil having 7 turns (N1), and an IPG 100 with a coil having 85 turns (N2), which corresponds to the highest matching distance having the fewest number of turns.

It should be noted that changing the number of turns in the coils will affect their inductance, which will in turn affect the frequency of the resonant circuits of which they are a part. Thus, modifying the number of turns will affect the communication frequency. However, should it be important to adjust this frequency after settling on the number of turns, the capacitances in the resonant circuits can thereafter be adjusted to bring the resonant frequency back to desired values.

Figure 7:
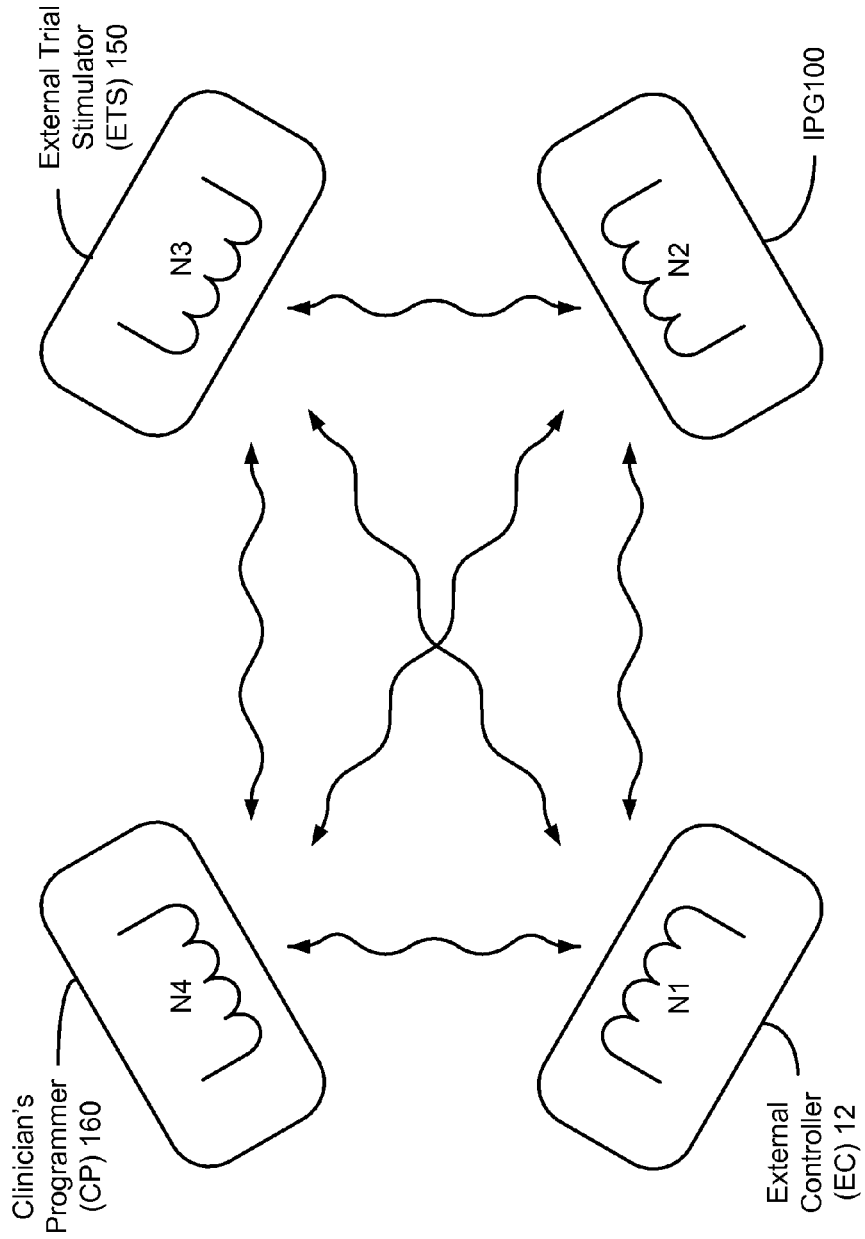
FIG. 7 shows a larger implantable medical device communication system comprising an external controller, an IPG, and external trial stimulator, and a clinician programmer.

Once communications between the EC 12 and the IPG 100 have been optimized in this fashion, further optimization can be accomplished to optimize communication with other devices in a broader implantable medical device system. FIG. 7 show such other devices, including an external trial stimulator (ETS) 150 and a clinician's programmer (CP) 160. As is well known, an ETS 150 is used after implantation of the electrode arrays 102 and 104 (FIG. 1A) in a patient. The ETS 150 couples to the implanted electrode arrays, and although it is not implanted in the patient, it generally mimics IPG operation. See, e.g., U.S. Patent Publication 2010/0228324. A clinician programmer 160 as its name suggests is typically used by a clinician in an office or operating room setting to communicate with either the ETS 150 or the IPG 100. The clinician programmer 160 can take the general shape of a wand for example. While it is not important to describe the ETS 150 or CP 160 in further detail, it suffices here to note that all of the devices shown in FIG. 7 are capable of communicating with each other using the same communications protocol, such as the FSK protocol mentioned earlier. Moreover, each contains a coil with a number of turns, and each will benefit from telemetry optimization. Specifically, the ETS 150's coil contains N3 turns, while the CP 160's coil contains N4 turns.

FIGS. 8A and 8B continue optimization using the result from simulation output 210 of FIG. 6, with the goal of optimizing the number of turns of coils in the ETS 150 (N3) and the CP 160 (N4). As noted earlier, simulation output 210 yielded particular optimal values for the number of turns in the EC 12 and the IPG 100, namely N1=7 and N2=85. These values, once set, can then be used to optimize communications with either the ETS 150 or the CP 160. For example, FIG. 8A shows a simulation output 220 geared at optimizing communications between the EC 12 and the ETS 150. In this case, the number of turns for the external controller has already been set (N1=7) by virtue of optimization with the IPG, and therefore the simulation output 220 does not reflect a change in that variable. Instead, the number of turns in the coil in the ETS 150 (N3) varies, and once again the simulated distances of communications in both directions between the ETS 150 and EC 12 are assessed to determine an element whose distances best match. As shown in FIG. 8A, this corresponds to N3=75 turns in the ETS 150.

FIG. 8B takes optimization one step further by optimizing the number of turns in the CP 160 (N4) based on the now-set values for any of N1, N2, and N3. Because the clinician's programmer 160 is most likely to communicate with either the IPG 100 or the ETS 150, either of these devices (and their set values for N1 and N3) are logically used during simulation to produce simulation output 230; FIG. 8B uses the ETS, and its set value of N3=75. Again, the simulated distances of communication in both directions between the ETS 150 and the CP 160 are assessed to determine an element in the simulation output 230 whose distances best match. As shown, this corresponds to N4=12 turns in the clinician's programmer. With N4 so determined, note that the sequence of the simulations outputs of FIGS. 6, 8A and 8B result in a system where the number of turns is optimized in each of the four devices shown in FIGS. 7: N1=7, N2=85, N3=75, and N4=12. (Note: FIGS. 8A and 8B, unlike FIG. 6, do not reflect the results of actual computerized simulations, but instead use fictional values to illustrate the extension of optimization to other components in the system).

To this point, each simulation has involved only two devices in the system. This optimizes the bidirectional communication distance between the two devices subject to the simulation, but does not establish a singular bidirectional communication distance for all devices in the system. For example, in FIG. 6, which simulated the EC 12 and the IPG 100, optimization of N1 and N2 set a maximum distance of about 60 inches between these devices. In FIG. 8A, which simulated the EC 12 and the ETS 150, optimization of N3 set a maximum distance of about 49 inches between these devices. In FIG. 8B, which simulated the ETS 150 and the CP 160, optimization of N4 set a maximum distance of about 45 inches between those devices. Each of these distances, while equal in both directions between the devices, is different for different pairs of devices.

FIGS. 9A and 9B address this issue, and illustrate simulation between three devices at one time, with the goal of establishing a single bidirectional communication distance. In the examples shown, the number of turns in the coils of three devices are simulated, and the results of such simulations are reflected in simulation outputs 240 and 250. Because three parameters are varying in these simulations, the simulation outputs 240 and 250 are 3-dimensional. The elements 205 each comprise additional values reflecting the fact that more than two devices are being optimized, and in FIGS. 9A and 9B different values are used, as will be explained shortly.

In FIG. 9A, the goal is to establish a single optimal maximum distance between the EC 12 and the IPG 100, and between the EC 12 and the ETS 100. As such, maximum distances are simulated for transmission from the EC 12 to the IPG 100 (dij) and in the opposite direction (dji), and for transmission from the EC 12 to the ETS 150 (dik) and in the opposite direction (dki), and each element 205 in simulation output 240 comprises each of these simulated values for a given N1, N2, and N3. Once simulation output 240 is populated with these values, the goal is to choose the element 205 whose values are the closest, e.g., having the smallest spread (e.g., standard deviation, or STD) in its four values, but the largest average value (MAX): MAX[AVG(dij, dji, dik, dki)] AND MIN[STD(dij, dji, dik, dki)]. The computer program in which the simulation output 240 is populated can be programmed to determine this element or a range of acceptable elements. There can be some subjectivity concerning what can comprise an optimal element: it may be more important for the average to be maximize even with some spread, or it may be more important that the spread be as small as possible, even if that the average distance is smaller. Designer preferences can therefore play into the selections of a suitable element. In any event, once an element 205 is chosen using objective and/or subjective criteria, and N1, N2, and N3 fixed on the basis of this choice, the result is essentially a single working maximum distance for the system, i.e., one maximum distance for telemetry between the EC 12 and the IPG 100, and between the EC 12 and the ETS 150.

Note that the simulation output 240 of FIG. 9A does not consider communications between the IPG 100 and the ETS 150, and so there would be no guarantee that the values chosen for N2 and N3 would provide optimal bidirectional communications between the IPG 100 and the ETS 150: that is, communications in one direction between these two devices may have a longer distance than in the other direction. This may be fine, particularly if the ETS 150 and the IPG 100 will not be expected to communicate with each other, or if they do so infrequently.

If however it is important to balance communications between three devices to determine a single maximum bidirectional distance between all three, the disclosed technique can be modified as shown in FIG. 9B. In FIG. 9B, the goal is to optimize communications between the EC 12, CP 160 and the IPG 100 by optimizing the number of turns in each (N1, N2, and N4). This may be a particularly useful simulation and optimization because these devices will all normally be expected to communicate with each other at significant distances, and it may therefore be desirable to know a single maximum distance for bidirectional communications between them regardless of which two of the three devices are communicating. As such, maximum distances are simulated for transmission from the EC 12 to the IPG 100 (dij) and in the opposite direction (dji), and for transmission from the EC 12 to the CP 160 (dil) and in the opposite direction (dli), and for transmission from the IPG 100 to the CP 160 (djl) and in the opposite direction (dlj). Each element 205 in simulation output 250 comprises each of these six simulated values for a given N1, N2, and N4. As with simulation output 240, once simulation output 250 is populated with these values, the goal is to choose the element 205 having the smallest spread but the largest average value (MAX): MAX[AVG(dij, dji, dil, dli, djl, dlj)] AND MIN[STD(dij, dji, dil, dli, djl, dlj)]. Determination of a single element, and hence optimal values for N1, N2, and N4, can once again be objectively determined by the computer program, perhaps in light of subjective criteria.

The techniques of FIGS. 9A and 9B can also be extended to the simulations optimization of the number of turns in four (or more) devices in the system, e.g., all of the EC 12, IPG 100, ETS 150, and CP 160, but this is not shown for convenience.

Figure 10:
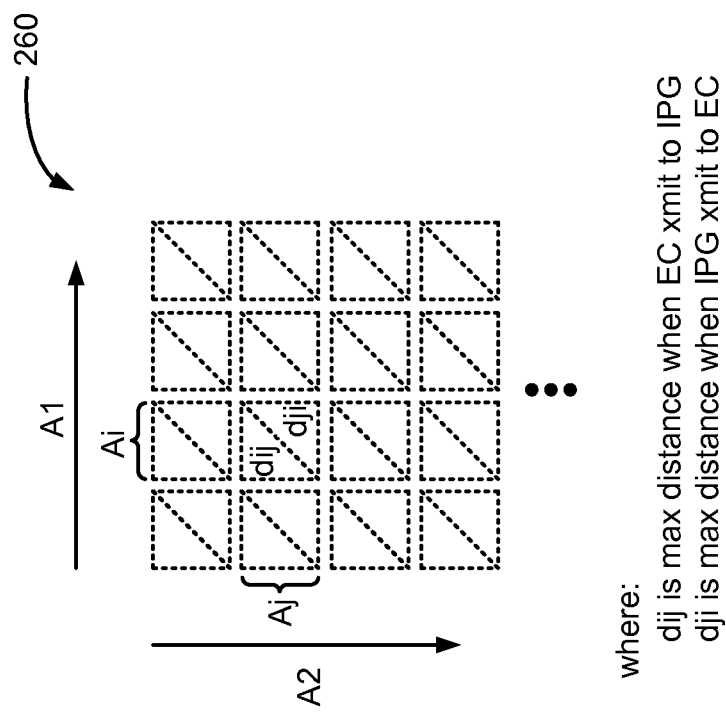
FIG. 10 shows a simulation output useable to select a different parameter, namely coil area, for bidirectional communication optimization.

To this point, optimization of bidirectional communication has focused on optimization of the number of turns in the coils in the devices involved. However, other parameters in the telemetry circuitry can also be subject to optimization with the goal of equating and maximizing the distance of communications in both directions. For example, in FIG. 10, output simulation 260 is geared toward optimization of the coil areas, A1 and A2 to achieve an equal and maximal bidirectional communication distance. Other parameters, such as Vo, Vt, or even other variables not disclosed here, could also be the subject of optimization, even if those parameters would be more difficult to change in a given system. Moreover, the parameter chosen need not be the same for each device considered. For example, the simulation output can be generated while varying the number of turns N1 in the external controller, and the area A2 of the coil 13 in the IPG 100. Still further, the parameters chosen for optimization may be from the same device, instead of one parameter from one device, and another parameter from the other device. Of course, when selecting the parameters for optimization during simulation, care should be taken to choose parameters which might affect the bidirectional communication distances differently, such that the simulation would be expected to yield useful information to balancing that distance.

While various embodiments have focused on optimizing parameters for which the maximum distances for an element in a matrix are closest and maximized, it should be understood that in some circumstances it may be more important to a given designer or in a given system to optimize only the maximum value of the maximum distances rather than its spread, or the closeness of the maximum distances despite whether the maximum distances are the longest. Therefore, the technique need not necessarily optimize both closeness and distance, but instead may determine optimal parameters by determining at least one element in a matrix for which the maximum distances are closest or maximized.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for optimizing wireless communications between first and second devices in an implantable medical device system, the first and second devices having first and second telemetry circuitries respectively, the method comprising:
   (a) performing a simulation in a computer system to determine an element, wherein the element comprises:
      a first maximum distance of wireless communications transmitted from a first antenna of the first telemetry circuitry and received at a second antenna of the second telemetry circuitry, and
      a second maximum distance of wireless communications transmitted from the second antenna of the second telemetry circuitry and received at the first antenna of the first telemetry circuitry,
      wherein the simulation occurs for a first parameter of the first telemetry circuitry and a second parameter of the second telemetry circuitry;
   (b) repeating step (a) to determine different elements at different values for the first parameter and the second parameter;
   (c) compiling the elements in a matrix in the computer system, with each element in the matrix comprising a first and second maximum distance for particular first and second parameters; and
   (d) determining optimal values for the first and second parameters by determining at least one element in the matrix for which the first and second maximum distances in the at least one element are closest to matching and maximized.

2. The method of claim 1, wherein the first antenna comprises a first coil, wherein the second antenna comprises a second coil, and wherein the first and second parameters respectively comprise a number of turns of the first and second coils.

3. The method of claim 2, wherein the optimal number of turns of the first and second coils further comprises a smallest number of turns of the first and second coils.

4. The method of claim 1, wherein step (d) is at least partially automated in the computer system.

5. The method of claim 1, wherein the first telemetry circuitry comprises a first receiver with a first threshold, the second telemetry circuitry comprises a second receiver with a second threshold, wherein the first maximum distance is determined by determining an input to the second receiver that equals the second threshold, and wherein the second maximum distance is determined by determining an input to the first receiver that equals the first threshold.

6. The method of claim 1, wherein the first device comprises an implantable medical device, and wherein the second device comprises an external controller for the implantable medical device.

7. The method of claim 1, wherein the first and second parameters are selected from the group consisting of a number of turns in a coil comprising the first and second antennas, an area of the first or second antennas, an output voltage of a transmitting telemetry coil, and an input threshold of a telemetry receiver.

8. The method of claim 1, further comprising optimizing wireless communications between the first device and a third device in an implantable medical device system, the third device having third telemetry circuitry, comprising:
(e) performing a simulation in a computer system to determine another element, wherein the another element comprises:
a third maximum distance of wireless communications transmitted from the first antenna of the first telemetry circuitry and received at a third antenna of the third telemetry circuitry, and
a fourth maximum distance of wireless communications transmitted from the third antenna of the third telemetry circuitry and received at the first antenna of the first telemetry circuitry,
wherein the simulation occurs for the optimal first parameter of the first telemetry circuitry and a third parameter of the third telemetry circuitry;
(f) repeating step (e) to determine different another elements at different values for the third parameter,
(g) compiling the another elements in another matrix in the computer system, with each element in the another matrix comprising a third and fourth maximum distance for the optimal first parameter and a particular third parameter; and
(h) determining an optimal value for the third parameter by determining at least one another element in the another matrix for which the third and fourth maximum distances in the at least one another element are closest to matching and maximized.

9. The method of claim 8, wherein the first device comprises an external controller for an implantable medical device, the second device comprises the implantable medical device, and the third device comprises an external trial stimulator.

10. A method for optimizing wireless communications between an implantable medical device and an external controller for the implantable medical device, the external controller having a first telemetry coil and the implantable medical device having a second telemetry coil, the method comprising:
(a) performing a simulation in a computer system to determine an element, wherein the element comprises:
a first maximum distance of wireless communications transmitted from the first telemetry coil and received at the second telemetry coil, and
a second maximum distance of wireless communications transmitted from the first telemetry coil and received at the first telemetry coil,
wherein the simulation occurs for a first number of turns of the first telemetry coil and a second number of turns of the second telemetry coil;
(b) repeating step (a) to determine different elements at different values for the first number of turns and the second number of turns;
(c) compiling the elements in a matrix in the computer system, with each element in the matrix comprising a first and second maximum distance for particular first and second numbers of turns; and
(d) determining optimal first and second numbers of turns by determining at least one element in the matrix for which the first and second maximum distances in the at least one element are closest to matching and maximized.

11. The method of claim 10, wherein the optimal number of turns of the first and second coils further comprises a smallest number of turns of the first and second coils.

12. The method of claim 10, wherein step (d) is at least partially automated in the computer system.

13. A method for optimizing wireless communications between devices in an implantable medical device system, each device having telemetry circuitry, the method comprising:
(a) performing a simulation in a computer system to determine an element comprising maximum distances of wireless communications in both directions between telemetry circuitry in each of the devices, wherein the simulation occurs for a given parameter of the telemetry circuitry in each of the devices;
(b) repeating step (a) to determine different elements at different values for the parameter in each of the devices;
(c) compiling the elements in a matrix in the computer system, with each element in the matrix comprising the maximum distances for particular of the parameters in each device; and
(d) determining optimal values for the parameters for each device by determining at least one element in the matrix for which the maximum distances in the at least one element are closest to matching and maximized.

14. The method of claim 13, wherein determining at least one element for which the maximum distances are closest to matching and maximized comprises determining at least one element with a largest average of maximum distances in the at least one element.

15. The method of claim 13, wherein determining at least one element for which the maximum distances are closest to matching and maximized comprises determining at least one element with a smallest spread of maximum distances in the at least one element.

16. The method of claim 15, wherein the spread comprises a standard deviation.

17. The method of claim 13, wherein the telemetry circuitry comprises a coil in each device, and wherein the parameter comprises a number of turns of the coil in each device.

18. The method of claim 17, wherein the optimal number of turns of the coil in each device further comprises a smallest number of turns of the coil in each device.

19. The method of claim 13, wherein step (d) is at least partially automated in the computer system.

20. The method of claim 13, wherein the devices are selected from the group consisting of an implantable medical device, an external controller for the implantable medical device, and external trial stimulator, and a clinician programmer.

21. The method of claim 13, wherein the parameter is one or more parameters selected from the group consisting of a number of turns in a telemetry coil, an area of a telemetry coil, an output voltage of a transmitting telemetry coil, and an input threshold of a telemetry receiver.

* * * * *